(12) United States Patent
Hayashi

(10) Patent No.: US 11,890,057 B2
(45) Date of Patent: Feb. 6, 2024

(54) GAZE DETECTION APPARATUS, GAZE DETECTION METHOD, AND GAZE DETECTION PROGRAM

(71) Applicant: JVCKENWOOD Corporation, Yokohama (JP)

(72) Inventor: Takahiro Hayashi, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 601 days.

(21) Appl. No.: 17/152,832

(22) Filed: Jan. 20, 2021

(65) Prior Publication Data

US 2021/0137378 A1 May 13, 2021

Related U.S. Application Data

(63) Continuation of application No. PCT/JP2019/021186, filed on May 29, 2019.

(30) Foreign Application Priority Data

Jul. 31, 2018 (JP) ................................. 2018-143732

(51) Int. Cl.
*A61B 3/00* (2006.01)
*A61B 3/113* (2006.01)
(Continued)

(52) U.S. Cl.
CPC ............. *A61B 3/152* (2013.01); *A61B 3/0025* (2013.01); *A61B 3/06* (2013.01); *A61B 3/113* (2013.01);
(Continued)

(58) Field of Classification Search
CPC ......... A61B 3/113; A61B 3/0025; A61B 3/06; A61B 3/152; A61B 3/0091; A61B 3/107;
(Continued)

(56) References Cited

U.S. PATENT DOCUMENTS

| | | |
|---|---|---|
| 2015/0199812 A1 | 7/2015 | Hakoshima et al. |
| 2016/0109945 A1 | 4/2016 | Kempinski |
| 2020/0183490 A1* | 6/2020 | Klingström ............... G06T 7/73 |

FOREIGN PATENT DOCUMENTS

| | | |
|---|---|---|
| JP | 08-321973 | 12/1996 |
| JP | 2014-71779 | 4/2014 |

OTHER PUBLICATIONS

Extended European Search Report for European Patent Application No. 19843409.4 dated Aug. 17, 2021.
(Continued)

*Primary Examiner* — Brandi N Thomas
(74) *Attorney, Agent, or Firm* — Amin, Turocy & Watson, LLP

(57) ABSTRACT

A gaze detection apparatus performs a calibration operation including displaying a target image in multiple positions on a display screen sequentially, setting, in the display screen, corresponding areas corresponding to the target images displayed on the display screen sequentially, and calculating positional data of points of regard in display periods in which the respective target images are displayed; and determines, with respect to each of the target images, whether the positional data of the point of regard that is calculated in the calibration operation is present within the corresponding area.

6 Claims, 9 Drawing Sheets

(51) Int. Cl.
*G06F 3/01* (2006.01)
*A61B 3/15* (2006.01)
*A61B 3/06* (2006.01)
*G06V 10/147* (2022.01)
*G06V 40/19* (2022.01)
*G06V 40/18* (2022.01)
*G06V 40/60* (2022.01)

(52) U.S. Cl.
CPC ............ *G06F 3/013* (2013.01); *G06V 10/147* (2022.01); *G06V 40/19* (2022.01); *G06V 40/193* (2022.01); *G06V 40/63* (2022.01)

(58) Field of Classification Search
CPC ....... A61B 3/112; A61B 3/14; A61B 17/0644; A61B 2090/365; A61B 3/08; A61B 5/103; A61B 5/4863; G06F 3/013; G06F 3/012; G06F 3/0346; G06F 3/038; G06F 3/011; G06F 3/017; G06F 1/163; G06F 18/00; G06F 2203/04806; G06F 3/03; G06F 3/0304; G06F 3/0425; G06F 3/04842; G06F 3/0485; G06F 3/0486; G06F 3/0488; G06F 3/14; G06F 3/147; G06V 40/193; G06V 40/19; G06V 10/147; G06V 40/63; G06V 10/245; G06V 40/161; G06V 40/165; G06V 40/171; G06V 40/20; G06V 20/20; G06V 40/113; G06T 2207/30201; G06T 7/73; G06T 2207/30041; G06T 2207/10012; G06T 7/13; G06T 7/60; G06T 7/74; G06T 7/254; G06T 7/85; G06T 17/00; G06T 7/0012; G06T 7/70
See application file for complete search history.

(56) References Cited

OTHER PUBLICATIONS

International Search Report and Written Opinion for International Application No. PCT/JP2019/021186 dated Aug. 20, 2019, 10 pages.

\* cited by examiner

GAZE DETECTION APPARATUS, GAZE DETECTION METHOD, AND GAZE DETECTION PROGRAM

CROSS-REFERENCE TO RELATED APPLICATION(S)

This application is a Continuation of PCT international application Ser. No. PCT/JP2019/021186 filed on May 29, 2019 which designates the United States, incorporated herein by reference, and which claims the benefit of priority from Japanese Patent Application No. 2018-143732, filed on Jul. 31, 2018, incorporated herein by reference.

BACKGROUND

1. Technical Field

The disclosure relates to a gaze detection apparatus, a gaze detection method, and a gaze detection program.

2. Description of the Related Art

A gaze detection apparatus that detects a position on an observation surface, such as a monitor screen, that an operator or a subject regards has been proposed. As a method of detecting a direction of a line of sight of a subject without wearing the device on the face, a technique of applying detection light to an eyeball of the subject, calculating a center of the pupil and a center of the corneal curvature from an image of the eye to which the detection light is applied, and detecting a vector toward the center of the pupil from the center of the corneal curvature as the direction of the line of sight of the subject is known. For such gaze detection apparatuses, a method of having an operator or a subject regard a target position on a monitor screen and performing calibration for each operator or subject in order to detect a line of sight of the subject or the operator more accurately has been proposed (For example, see Japanese Laid-open Patent Publication No. H8-321973).

According to H8-321973, when an error occurs in a calibration operation, a notification of the error is made and a return to the default state for performing the calibration operation again is made. In order to perform the calibration operation again thereafter, however, the operator, or the like, has to make manual inputs. For this reason, depending on the subject, the concentration may scatter and the accuracy of detection may lower.

SUMMARY

The disclosure was made in view of the above-described circumstances and an object of the disclosure is to provide a gaze detection apparatus, a gaze detection method, and a gaze detection program that make it possible to inhibit accuracy of detection from lowering.

A gaze detection apparatus according to the present disclosure comprising: a display screen on which an image is displayed; a light source configured to apply detection light to at least one of eyeballs of a subject; an image data acquisition unit configured to acquire image data on the eyeball to which the detection light is applied; a position detector configured to detect, from the acquired image data, positional data of a pupil center representing a center of a pupil of the eyeball to which the detection light is applied and positional data of a corneal reflection center representing a center of corneal reflection; a point-of-regard detector configured to calculate, based on a position of the pupil center and a position of the corneal reflection center, positional data of a point of regard of the subject on a plane containing the display screen; and a controller configured to perform a calibration operation including displaying a target image in multiple positions on the display screen sequentially, setting, in the display screen, corresponding areas corresponding to the target images displayed on the display screen sequentially, and calculating positional data of the points of regard in display periods in which the respective target images are displayed; determine, with respect to each of the target images, whether the positional data of the point of regard that is calculated in the calibration operation is present within the corresponding area; when the number of valid target images that are the target images on each of which it is determined that the positional data of the point of regard is present within the corresponding area is at or above a threshold, output the positional data of the points of regard of the valid target images as calibration data; and, when the number of the valid target images is under the threshold, cause the calibration operation to be repeated.

A gaze detection method according to the present disclosure comprising: applying detection light to at least one of eyeballs of a subject; acquiring image data on the eyeball to which the detection light is applied; detecting, from the acquired image data, positional data of a pupil center representing a center of a pupil of the eyeball to which the detection light is applied and positional data of a corneal reflection center representing a center of corneal reflection; calculating, based on a position of the pupil center and a position of the corneal reflection center, positional data of a point of regard of the subject on a plane containing a display screen; and performing a calibration operation including displaying a target image in multiple positions on the display screen sequentially, setting, in the display screen, corresponding areas corresponding to the target images displayed on the display screen sequentially, and calculating positional data of the points of regard in display periods in which the respective target images are displayed; determining, with respect to each of the target images, whether the positional data of the point of regard that is calculated in the calibration operation is present within the corresponding area; when the number of valid target images that are the target images on each of which it is determined that the positional data of the point of regard is present within the corresponding area is at or above a threshold, outputting the positional data of the points of regard of the valid target images as calibration data; and, when the number of the valid target images is under the threshold, causing the calibration operation to be repeated.

A non-transitory computer readable recording medium storing therein a gaze detection program according to the present disclosure that causes a computer to execute a process including: applying detection light to at least one of eyeballs of a subject; acquiring image data on the eyeball to which the detection light is applied; detecting, from the acquired image data, positional data of a pupil center representing a center of a pupil of the eyeball to which the detection light is applied and positional data of a corneal reflection center representing a center of corneal reflection; calculating, based on a position of the pupil center and a position of the corneal reflection center, positional data of a point of regard of the subject on a plane containing a display screen; and performing a calibration operation including displaying a target image in multiple positions on the display screen sequentially, setting, in the display screen, corresponding areas corresponding to the target images displayed on the display screen sequentially, and calculating positional data of the points of regard in display periods in which the respective target images are displayed; determining, with respect to each of the target images, whether the positional data of the point of regard that is calculated in the calibration operation is present within the corresponding area; when the number of valid target images that are the target images on each of which it is determined that the positional data of the point of regard is present within the corresponding area is at or above a threshold, outputting the positional data of the points of regard of the valid target images as calibration data; and, when the number of the valid target images is under the threshold, causing the calibration operation to be repeated.

DETAILED DESCRIPTION OF THE PREFERRED EMBODIMENTS

An embodiment of a gaze detection apparatus, a gaze detection method, and a gaze detection program of the disclosure will be described based on the drawings. The embodiment does not limit the invention. The components in the embodiment described below include ones that are replaceable by those skilled in the art and that are easily replaceable or ones that are substantially the same.

In the following description, a three-dimensional global coordinate system is set and a positional relationship of each unit will be described. A direction parallel to a first axis of a given surface serves as an X-axis direction, a direction parallel to a second axis of a given surface orthogonal to the first axis serves as a Y-axis direction, and a direction parallel to a third axis orthogonal to each of the first axis and the second axis serves as a Z-axis direction. The given surface contains an X-Y plane.

Gaze Detection Apparatus

Figure 1:
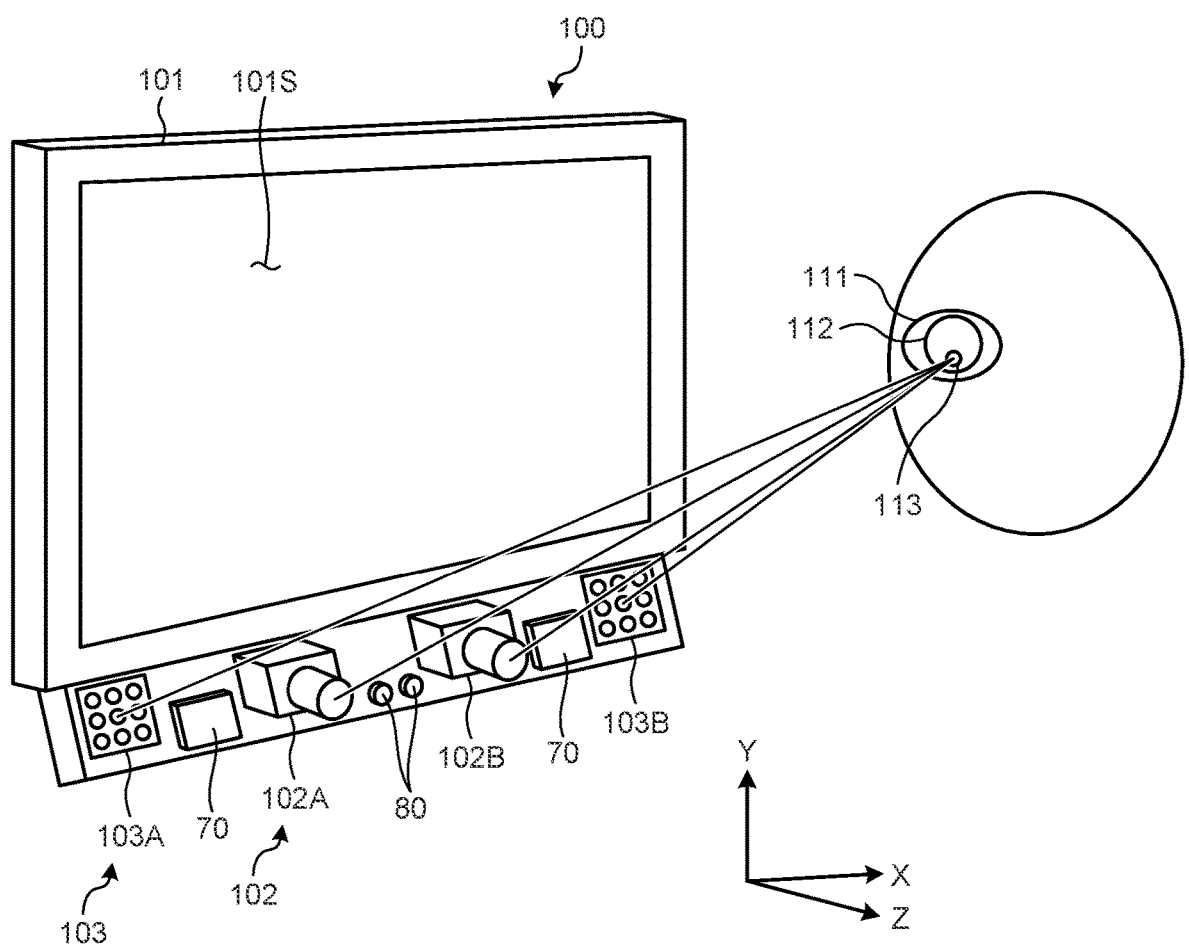
FIG. 1 is a perspective view schematically illustrating an example of a gaze detection apparatus according to an embodiment.

FIG. 1 is a perspective view schematically illustrating an example of a gaze detection apparatus 100 according to a first embodiment. As illustrated in FIG. 1, the gaze detection apparatus 100 includes a display device 101, a stereo camera device 102, and an illumination device 103.

The display device 101 contains a flat panel display, such as a liquid crystal display (LCD) or an organic electroluminescence display (OLED). In the embodiment, the display device 101 includes a display screen 101S. The display screen 101S displays an image. In the embodiment, the display device 101S displays, for example, an index for evaluating the visual function of a subject. The display screen 101S is substantially parallel to the X-Y plane. The X-axis direction is the horizontal direction of the display screen 101S, the Y-axis direction is the vertical direction of the display screen 101S, and the Z-axis direction is a depth direction orthogonal to the display screen 101S.

The stereo camera device 102 includes a first camera 102A and a second camera 102B. The stereo camera device 102 is arranged below the display screen 101S of the display device 101. The first camera 102A and the second camera 102B are arranged in the X-axis direction. The first camera 102A is arranged in a negative X-direction with respect to the second camera 102B. Each of the first camera 102A and the second camera 102B contains an infrared camera and includes an optical system capable of transmitting infrared light having a wavelength of, for example, 850 [nm] and an imaging device capable of receiving the infrared light.

The illumination device (light source) 103 includes a first light source 103A and a second light source 103B. The illumination device 103 is arranged below the display screen 101S of the display device 101. The first light source 103A and the second light source 103B are arranged in the X-axis direction. The first light source 103A is arranged in the negative X-direction with respect to the first camera 102A. The second light source 103B is arranged in the positive X-axis direction with respect to the second camera 102B. Each of the first light source 103A and the second light source 103B contains a light emitting diode (LED) light source and is capable of emitting infrared light of a wavelength of, for example, 850 [nm]. The first light source 103A and the second light source 103B may be arranged between the first camera 102A and the second camera 102B. Alternatively, the stereo camera 102 may be arranged above the display screen 101S of the display device 101.

The illumination device 103 emits infrared light that is detection light, thereby illuminating an eyeball 111 of the subject. The stereo camera device 102 captures an image of part of the eyeball 111 (collectively referred to as an "eyeball") with the second camera 102B when the detection light that is emitted from the first light source 103A is applied to the eyeball 111 and captures an image of the eyeball 111 with the first camera 102A when detection light that is emitted from the second light source 103B is applied to the eyeball 111.

A frame synchronization signal is output from at least one of the first camera 102A and the second camera 102B. The first light source 103A and the second light source 103B emit detection light based on the frame synchronization signal. The first camera 102A captures image data on the eyeball 111 when detection light that is emitted from the second light source 103B is applied to the eyeball 111. The second camera 102B captures image data of the eyeball 111 when detection light that is emitted from the first light source 103A is applied to the eyeball 111.

When the detection light is applied to the eyeball 111, part of the detection light reflects on a pupil 112 and the light from the pupil 112 is incident on the stereo camera device 102. When the detection light is applied to the eyeball 111, a corneal reflection image 113 that is a virtual image of the cornea is formed on the eyeball 111 and the light from the corneal reflection image 113 is incident on the stereo camera device 102.

Appropriately setting relative positions among the first camera 102A, the second camera 102B, the first light source 103A, and the second light source 103B lowers the intensity of light that is incident on the stereo camera device 102 from the pupil 112 to the stereo camera device 102 and increases the intensity of light that is incident on the stereo camera device 102 from the corneal reflection image 113. In other words, an image of the pupil 112 that is captured by the stereo camera device 102 has a low brightness and an image of the corneal reflection image 113 has a high brightness. The stereo camera device 102 is able to detect a position of the pupil 112 and a position of the corneal reflection image 113 based on the brightness of the captured images.

Figure 2:
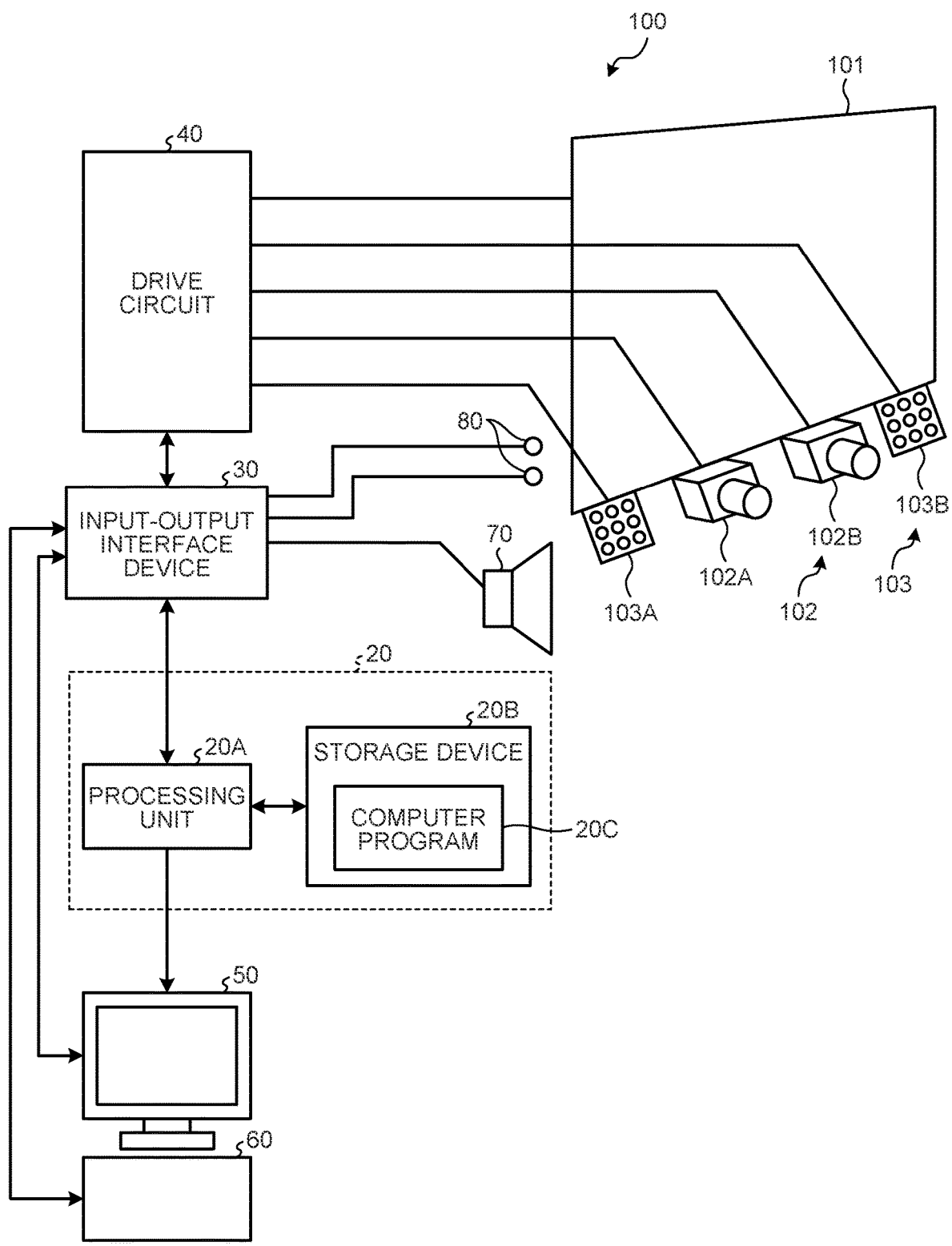
FIG. 2 is a diagram illustrating an example of a hardware configuration of the gaze detection apparatus according to the embodiment.

FIG. 2 is a diagram illustrating an example of a hardware configuration of the gaze detection apparatus 100 according to the embodiment. As illustrated in FIG. 2, the gaze detection apparatus 100 includes the display device 101, the stereo camera device 102, the illumination device 103, a computer system (controller) 20, an input-output interface device 30, a drive circuit 40, an output device 50, and an input device 60.

The computer system 20, the drive circuit 40, the output device 50, and the input device 60 communicate data via the input-output interface device 30. The computer system 20 contains a processing unit 20A and a storage device 20B. The processing unit 20A contains a microprocessor, such as a central processing unit (CPU). The storage device 20B contains a memory, such as a read only memory (ROM) and a random access memory (RAM), or a storage. The processing unit 20A performs operations according to a computer program 20C that is stored in the storage device 20B.

The drive circuit 40 generates drive signals and outputs the drive signals to the display device 101, the stereo camera device 102, and the illumination device 103. The drive circuit 40 supplies image data on the eyeball 111 that is captured with the stereo camera device 102 to the computer system 20 via the input-output interface device 30.

The output device 50 contains a display device, such as a flat panel display. Note that the output device 50 may contain a printing device. The input device 60 is operated and thus generates input data. The input device 60 contains a keyboard or a mouse for the computer system. Note that the input device 60 may contain a touch sensor that is provided on a display screen of the output device 50 that is a display device.

In the embodiment, the display device 101 and the computer system 20 are independent devices. Note that the display device 101 and the computer system 20 may be integrated. For example, when the gaze detection apparatus 100 contains a tablet personal computer, the computer system 20, the input-output interface device 30, the drive circuit 40, and the display device 101 may be mounted on the tablet personal computer.

Figure 3:
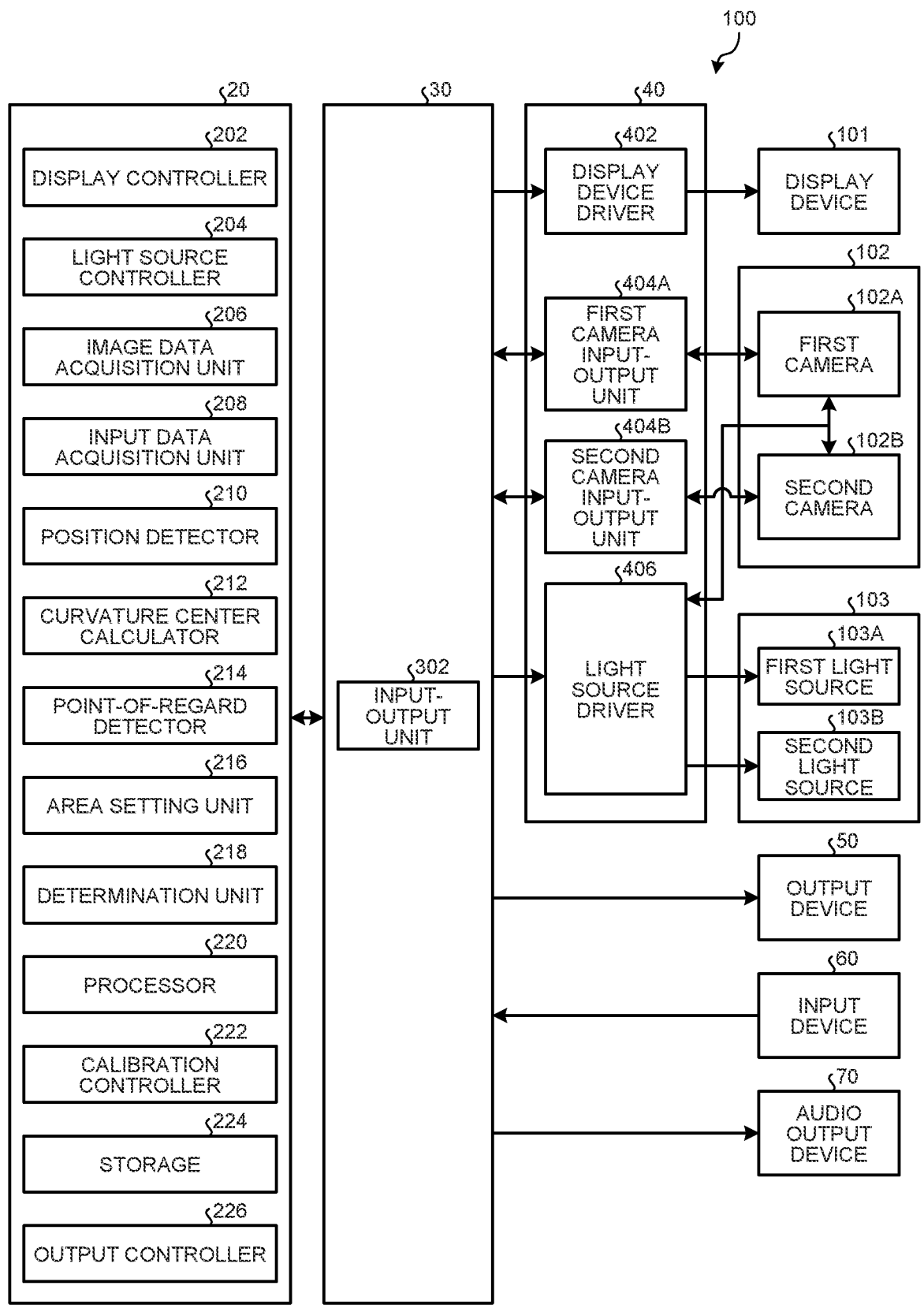
FIG. 3 is a functional block diagram representing an example of the gaze detection apparatus according to the embodiment.

FIG. 3 is a functional block diagram illustrating an example of the gaze detection apparatus 100 according to the embodiment. As illustrated in FIG. 3, the input-output interface device 30 includes an input-output unit 302. The drive circuit 40 includes a display device driver 402 that generates a drive signal for driving the display device 101 and outputs the drive signal to the display device 101; a first camera input-output unit 404A that generates a drive signal for driving the first camera 102A and outputs the drive signal to the first camera 102A; a second camera input-output unit 404B that generates a drive signal for driving the second camera 102B and outputs the drive signal to the second camera 102B; and a light source driver 406 that generates dive signals for driving the first light source 103A and the second light source 103B and outputs the drive signals to the first light source 103A and the second light source 103B. The first camera input-output unit 404A supplies image data on the eyeball 111 that is captured by the first camera 102A to the computer system 20 via the input-output unit 302. The second camera input-output unit 404B supplies the image data on the eyeball 111 that is captured by the second camera 102B to the computer system 20 via the input-output unit 302.

The computer system 20 controls the gaze detection apparatus 100. The computer system 20 includes a display controller 202, a light source controller 204, an image data acquisition unit 206, an input data acquisition unit 208, a position detector 210, a curvature center calculator 212, a point-of-regard detector 214, an area setting unit 216, a determination unit 218, a processor 220, a calibration controller 222, a storage 224, and an output controller 226. The functions of the computer system 20 are implemented by the processing unit 20A and the storage device 20B.

The display controller 202 displays an image to be shown to the subject on the display screen 101S of the display device 101. The display controller 202 is capable of displaying, for example, a target image in a calibration operation in multiple positions (target positions) on the display screen 101S. The display controller 202 may display the target image in each of the target positions such that the target image switches sequentially or display the target image such that the target image shifts sequentially to the target positions within the display screen 101S. The number of target positions in which the target image is displayed can be, for example, set by the operator by making an input via the input device 60, or the like.

The light source controller 204 controls the light source driver 406, thereby controlling the operational state of the first light source 103A and the second light source 103B. The light source controller 204 controls the first light source 103A and the second light source 103B such that the first light source 103A and the second light source 103B emit detection light at different sets of timing.

The image data acquisition unit 206 acquires image data on the eyeball 111 of the subject of which image is captured by the stereo camera device 102 including the first camera 102A and the second camera 102B from the stereo camera device 102 via the input-output unit 302.

The input data acquisition unit 208 acquires the input data that is generated by operating the input device 60 from the input device 60 via the input-output unit 302.

The position detector 210 detects positional data of a pupil center based on the image data on the eyeball 111 that is acquired by the image data acquisition unit 206. Based on the image data of the eyeball 111 that is acquired by the image data acquisition unit 206, the position detector 210 detects positional data of a corneal reflection center. The pupil center is the center of the pupil 112. The corneal reflection center is the center of the corneal reflection image 113. The position detector 210 detects the positional data of the pupil center and the positional data of the corneal reflection center with respect to the eyeball 111 to which the detection light is applied.

Based on the image data on the eyeball 111 that is acquired by the image data acquisition unit 206, the curvature center calculator 212 calculates positional data of the center of corneal curvature of the eyeball 111.

Based on the image data on the eyeball 111 that is acquired by the image data acquisition unit 206, the point-of-regard detector 214 detects positional data of the point of regard of the subject. In the embodiment, the positional data of the point of regard refers to positional data of the intersection between a line-of-sight vector of the subject that is defined by the three-dimensional global coordinate system and a plane containing the display screen 101S of the display device 101. Based on the positional data of the pupil center and the positional data of the center of corneal curvature that are acquired from the image data on the eyeball 111, the point-of-regard detector 214 detects a light-of-sight vector of each of the left and right eyeballs 111. After the line-of-sight vector is detected, the point-of-regard detector 214 detects the positional data of the point of regard representing the intersection between the line-of-sight vector and the display screen 101S.

In a display period in which the target image is displayed on the display screen 101S, the area setting unit 216 sets a corresponding area corresponding to the target image that is displayed on the display screen 101S.

In the display period in which the target image is made on the display screen 101S, the determination unit 218 determines whether the point of regard is present within the corresponding area. The determination unit 218 determines whether the point of regard is present within the corresponding area, for example, regularly at given intervals. The given interval may be, for example, the period of the frame synchronization signal (for example, every 50 [msec]) that is output from the first camera 102A and the second camera 102B.

Based on data on the determination by the determination unit 218, the processor 220 counts the number of times it is determined that the point of regard is present within the corresponding area. The processor 220 includes a counter that counts, for the corresponding area, the number of times the determination is made.

The calibration controller 222 causes the calibration operation to be performed. The calibration operation includes displaying a target image in multiple positions on the display screen 101S, setting a corresponding area corresponding to the target image that is displayed on the display screen 101S on the display screen 101S, and calculating positional data of a point of regard in a display period in which each target image is displayed.

The calibration controller 222 determines, with respect to each target image, whether the positional data of the point of regard that is calculated in the calibration operation is present within the corresponding area. When performing the determination, the calibration controller 222 determines, with respect to each target image, whether the point of regard is present within the corresponding area based on the number of times the determination is made that is counted by the processor 220. For example, with respect to each target image, when the number of times it is determined that the point of regard is present within the corresponding area is at or above a given ratio to the number of sets of detection of positional data of the point of regard, the calibration controller 222 determines that the point of regard is present within the corresponding area with respect to the target image. A target image on which it is determined that the positional data of the point of regard is present within the corresponding area is referred to as a valid target image below. With respect to each target image, when the number of times it is determined that the point of regard is present within the corresponding area is under the given ratio to the number of sets of detection of positional data of the point of regard, the calibration controller 222 determines that the point of regard is not present within the corresponding area with respect to the target area.

The calibration controller 222 determines whether the number of valid target image is at or above a threshold. The threshold can be set, for example, by the operator by making an input via the input device 60, or the like. When the number of valid target images is at or above the threshold, the calibration controller 222 outputs the positional data of the points of regard with respect to the valid target images as calibration data. When the number of valid target images is under the threshold, the calibration controller 222 causes the calibration operation to be repeated.

When causing the calibration operation to be repeated, the calibration controller 222 displays a target image in each of the same multiple target positions as those in the latest calibration operation and, when the target image that is displayed in the target position that is the same between the repeated calibration operation and the latest calibration operation or a calibration operation before the latest calibration operation is successively determined as a valid target image, determines other all valid target images in the latest calibration operation or a calibration operation before the latest calibration operation among the successive calibration operations as valid target images in the repeated calibration operation.

When causing the calibration operation to be repeated, the calibration controller 222 is able to display a target image whose appearance differs from that of the target image that is displayed in the latest calibration operation. In this case, for example, based on an instruction of the calibration controller 222, the display controller selects one of multiple types of target images and displays the selected one.

When the calibration operation is performed for a given number of times and the number of valid target images is under the threshold in every calibration operation, the calibration controller 222 makes an output indicating that the calibration operation is erroneous. The given number of times the calibration operation is caused to be performed can be set, for example, by the operator by making an input via the input device 60, or the like.

The storage 224 stores various types of data and programs on the above-described gaze detection. The storage 224 stores display data (images, videos, etc.) corresponding to the number of positions in which the target image is displayed. The storage 224 stores, for example, the display data on multiple types of target images with different appearances. The storage 224 stores positional data of the point of regard that is calculated in each calibration operation.

The storage 224 stores a gaze detection program that causes a computer to execute a process of applying detection light to at least one of eyeballs of a subject; a process of acquiring image data on the eyeball to which the detection light is applied; a process of detecting, from the acquired image data, positional data of a pupil center representing a center of a pupil of the eyeball to which the detection light is applied and positional data of a corneal reflection center representing a center of corneal reflection; a process of calculating positional data of a point of regard of the subject on a plane containing a display screen based on a position of the pupil center and a position of the corneal reflection center; and a process of performing a calibration operation including sequentially displaying a target image in multiple positions on the display screen, sequentially setting, in the display screen, corresponding areas corresponding to the target images displayed on the display screen, and calculating positional data of the point of regard in a display period during which each of the target images is displayed; determining, with respect to each of the target images, whether the positional data of the point of regard that is calculated in the calibration operation is present within the corresponding area; when the number of valid target images that are target images on each of which it is determined that the positional data of the point of regard is present within the corresponding area is at or above a threshold, outputting the positional data of the points of regard with respect to the valid images as calibration data; and, when the number of valid images is under the threshold, causing the calibration operation to be repeated.

The output controller 226 outputs data to at least one of the display device 101 and the output device 50.

Figure 4:
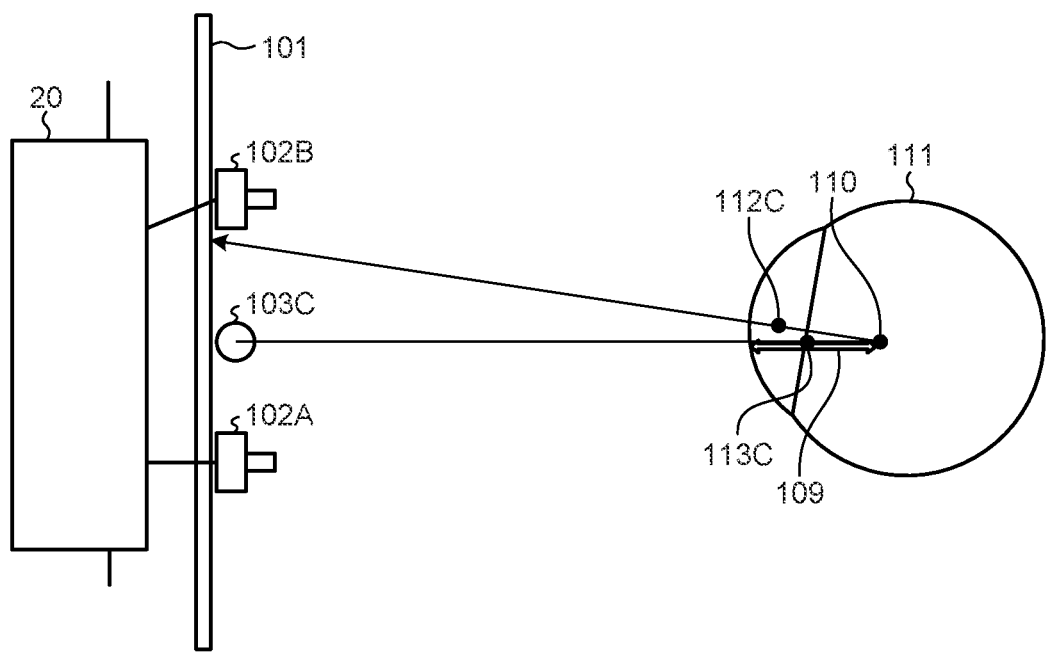
FIG. 4 is a schematic diagram for explaining a method of calculating positional data on the center of a corneal curvature according to the embodiment.
Figure 5:
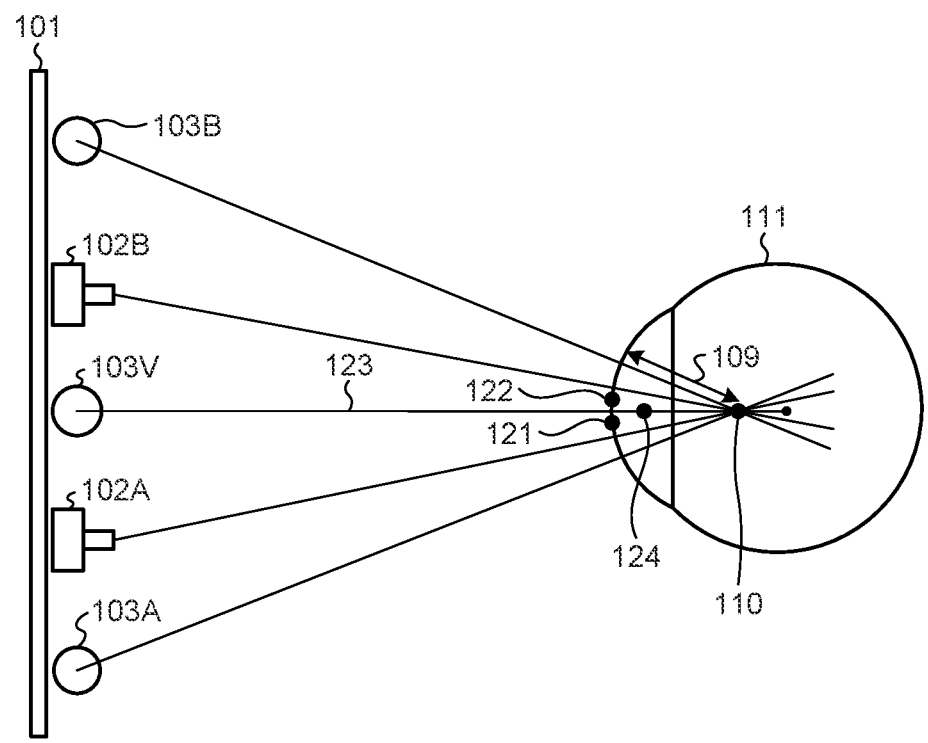
FIG. 5 is a schematic diagram for explaining the method of calculating positional data on the center of a corneal curvature according to the embodiment.

An overview of a process performed by the curvature center calculator 212 will be described. The curvature center calculator 212 calculates positional data of the center of corneal curvature of the eyeball 111 based on the image data on the eyeball 111. FIGS. 4 and 5 are schematic diagrams for explaining a method of calculating positional data of a corneal curvature center 110 according to the embodiment. FIG. 4 illustrates an example in which the eyeball 111 is illuminated with a single light source 103C. FIG. 5 illustrates an example in which the eyeball 111 is illuminated with the first light source 103A and the second light source 103B.

First of all, the example illustrated in FIG. 4 will be described. The light source 103C is arranged between the first camera 102A and the second camera 102B. A pupil center 112C is the center of the pupil 112. A corneal reflection center 113C is the center of the corneal reflection image 113. In FIG. 4, the pupil center 112C represents the center of the pupil at the time when the eyeball 111 is illuminated with the single light source 103C. The corneal reflection center 113C represents the center of corneal reflection at the time when the eyeball 111 is illuminated with the single light source 103C. The corneal reflection center 113C is present on a straight line connecting the light source 103C and the corneal curvature center 110. The corneal reflection center 113C is positioned at an intermediate point between the surface of the cornea and the corneal curvature center 110. A corneal curvature radius 109 is a distance between the surface of the cornea and the corneal curvature center 110. Positional data of the corneal reflection center 113C is detected by the stereo camera device 102. The corneal curvature center 110 is present on a straight line connecting the light source 103C and the corneal reflection center 113C. The corneal curvature center calculator 212 calculates, as positional data of the corneal curvature center 110, positional data that makes the distance from the corneal reflection center 113C on the straight line be at a given value. The given value is a value that is determined previously from a value of a general corneal curvature radius and the given value is stored in the storage 224.

The example illustrated in FIG. 5 will be described. In the embodiment, the first camera 102A and the second light source 103B and the second camera 102B and the first light source 103A are arranged at horizontally symmetrical positions with respect to a straight line passing through the intermediate position between the first camera 102A and the second camera 102B. It can be thought that a virtual light source 103V is in the intermediate position between the first camera 102A and the second camera 102B. A corneal reflection center 121 represents a center of corneal reflection in an image of the eyeball 111 that is captured with the second camera 102B. A corneal reflection center 122 represents a center of corneal reflection in an image of the eyeball 111 that is captured with the first camera 102A. A corneal reflection center 124 represents a center of corneal reflection corresponding to the virtual light source 103V. Positional data of the corneal reflection center 124 is calculated based on positional data of the corneal reflection center 121 and positional data of the corneal reflection center 122. The stereo camera device 102 detects the positional data of the corneal reflection center 121 and the positional data of the corneal reflection center 122 in the three-dimensional local coordinate system that is defined in the stereo camera device 102. For the stereo camera device 102, camera calibration by a stereo calibration method is performed previously and a conversion parameter to convert the three-dimensional local coordinate system into a three-dimensional global coordinate system is calculated. The conversion parameter is stored in the storage 224. Using the conversion parameter, the curvature center calculator 212 converts the positional data of the corneal reflection center 121 and the positional data of the corneal reflection center 122 into positional data in the three-dimensional global coordinate system. Based on the positional data of the corneal reflection center 121 and the positional data of the corneal reflection center 122 that are defined in the three-dimensional global coordinate system, the curvature center calculator 212 calculates the positional data of the corneal reflection center 124 in the three-dimensional global coordinate system. The corneal curvature center 110 is on a straight line 123 connecting the virtual light source 103V and the corneal reflection center 124. The curvature center calculator 212 calculates the positional data that makes the distance from the corneal reflection center 124 on the straight line 123 be a given value as the positional data of the corneal curvature center 110. The given value is a value that is determined previously from a value of a general corneal curvature radius and the given value is stored in the storage 224.

As described above, even when there are two light sources, the corneal curvature center 110 is calculated in the same manner as that in the case of a single light source.

The corneal curvature radius 109 is the distance between the surface of the cornea and the corneal curvature center 110. By calculating the positional data of the surface of the cornea and the positional data of the corneal curvature center 110, the corneal curvature radius 109 is calculated.

Gaze Detection Method

Figure 6:
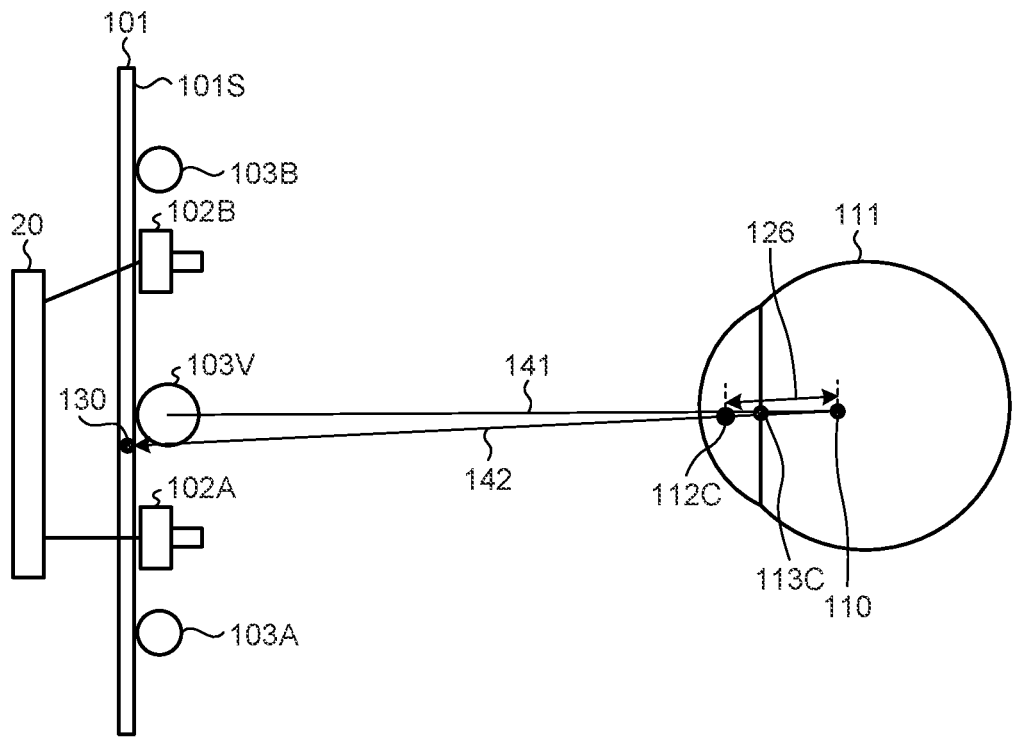
FIG. 6 is a schematic diagram for explaining an example of a calibration process according to the embodiment.

An example of the gaze detection method according to the embodiment will be described. In the gaze detection method according to the embodiment, after performing the calibration process, a process of detecting a point of regard is performed. FIG. 6 is a schematic diagram for explaining an example of the calibration process according to the embodiment. In the calibration process, a target position 130 is set for a subject to regard. The target position 130 is defined in the three-dimensional global coordinate system. The display controller 202 displays a target image in the target position 130. A straight line 141 is a straight line connecting the virtual light source 103V and the corneal reflection center 113C. A straight line 142 is a straight line connecting the target position 130 and the pupil center 112C. The corneal curvature center 110 is the intersection between the straight line 141 and the straight line 142. The corneal curvature center calculator 212 is able to calculate positional data of the corneal curvature center 110 based on positional data of the virtual light source 103V, positional data of the target position 130, positional data of the pupil center 112C, and positional data of the corneal reflection center 113C. The point-of-regard detector 214 is able to calculate positional data of the point of gaze from the calculated center of corneal curvature. Details of the calibration process will be described below.

Figure 7:
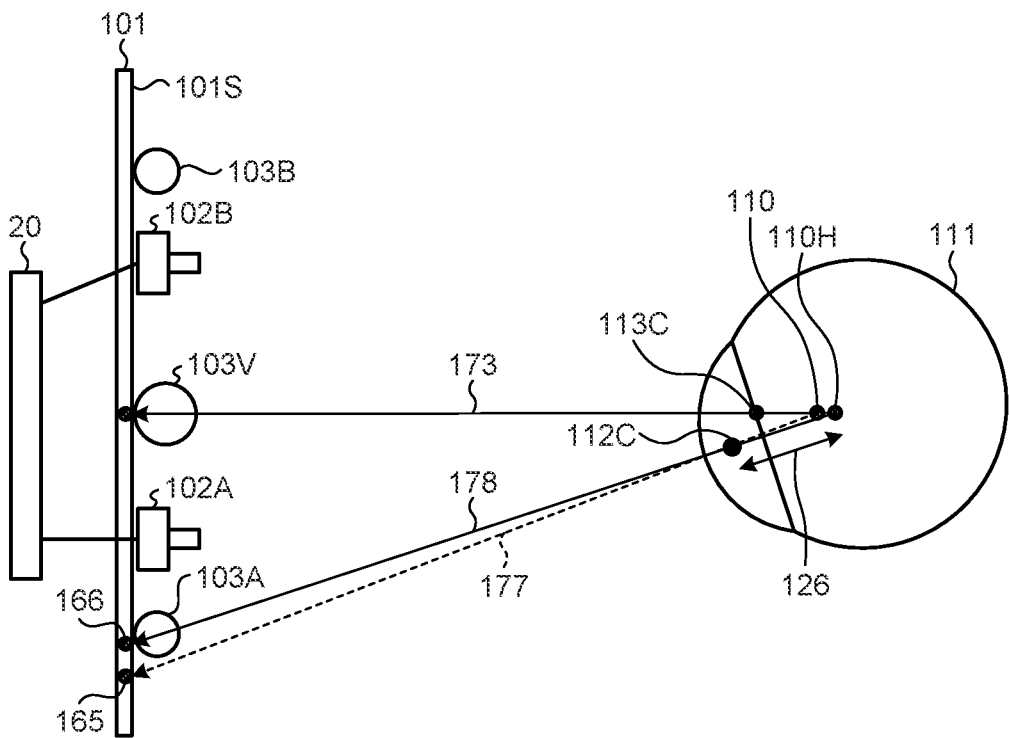
FIG. 7 is a schematic diagram for explaining an example of a point-of-regard detection process according to the embodiment.

A point-of-regard detection process will be described. The point-of-regard detection process is performed after the calibration process. Based on the image data on the eyeball 111, the point-of-regard detector 214 calculates a line-of-sight vector of the subject and positional data of the point of regard. FIG. 7 is a schematic view for explaining an example of the point-of-regard detection process according to the embodiment. In FIG. 7, a point of regard 165 represents a point of regard that is calculated from the corneal curvature center that is calculated using the value of a general curvature radius. A point of regard 166 represents a point of regard that is calculated from a center of corneal curvature that is calculated from the corneal curvature center that is calculated using a distance 126 that is calculated in the calibration process. The pupil center 112C represents the center of the pupil that is calculated in the calibration process and the corneal reflection center 113C represents the center of corneal reflection that is calculated in the calibration process. A straight line 173 is a straight line connecting the virtual light source 103V and the corneal reflection center 113C. The corneal curvature center 110 is the position of the corneal curvature center that is calculated from the value of a general curvature radius. The distance 126 is the distance between the pupil center 112C and the corneal curvature center 110 that are calculated by the calibration process. A corneal curvature center 110H represents the position of the post-correction corneal curvature center obtained by correcting the corneal curvature center 110 using the distance 126. The corneal curvature center 110H is calculated from the fact that the corneal curvature center 110 is on the straight line 173 and that the distance between the pupil center 112C and the corneal curvature center 110 is the distance 126. Accordingly, a line of sight 117 that is calculated in the case where a general curvature radius is used is corrected into a line of sight 178. The point of regard on the display screen 101S of the display device 101 is corrected from the point of regard 165 to a point of regard 166.

Calibration Process

Figure 8:
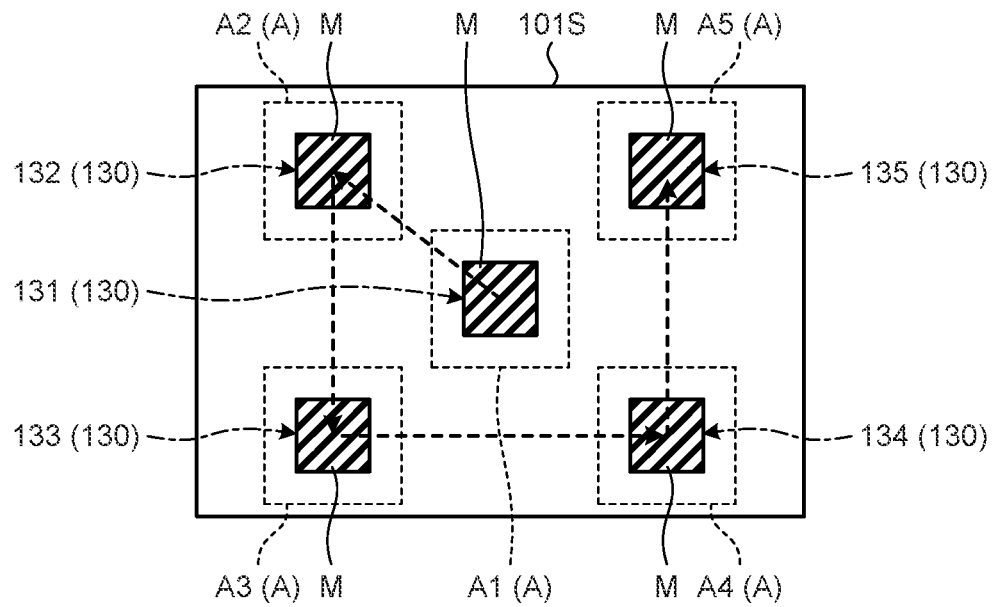
FIG. 8 is a diagram illustrating a display example in which a target image is displayed on a display screen.

The calibration process described above will be described. In the calibration process, the display controller 202 displays a target image in multiple target positions. FIG. 8 is a diagram illustrating a display example in which a target image M is displayed on the display screen 101S. As illustrated in FIG. 8, the display controller 202 displays the target image M in the target positions 130 sequentially. The number of the target positions 130 in which the target image M is displayed can be set by the operator previously via the input device 60, or the like. The display controller 202 displays the target images M sequentially in the set number of the target positions 130 one by one. For example, when the number of the target positions 130 is set at "5", as illustrated in FIG. 8, the display controller 202 displays the target image M in each of five target positions 130 that are a first position 131, a second position 132, a third position 133, a fourth position 134, and a fifth position 135 on the display screen 101S such that the target image switches sequentially. FIG. 8 represents the five target images M on the five target positions 130 and, practically, the single target image M is sequentially displayed in each target position. The display controller 202 displays the target image M such that the period of display is equal among the target positions 130.

The area setting unit 216 sets a corresponding area A corresponding to the target image M that is displayed on the display screen 101S. As illustrated in FIG. 8, when the target image M is displayed on the five target positions 130 from the first position 131 to the fifth position 135, the area setting unit 216 sets corresponding areas A corresponding to the respective target images M in the display periods in which the respective target positions 130 are displayed. For example, the area setting unit 216 sets a corresponding area A1 corresponding to the target image M in the first position 131 in the display period in which the target image M is displayed in the first position 131. In the display period in which the target image M is displayed in the second position 132, the area setting unit 216 sets a corresponding area A2 corresponding to the target image M in the second position 132. In the display period in which the target image M is displayed in the third position 133, the area setting unit 216 sets a corresponding area A3 corresponding to the target image M in the third position 133. In the display period in which the target image M is displayed in the fourth position 134, the area setting unit 216 sets a corresponding area A4 corresponding to the target image M in the fourth position 134. In the display period in which the target image M is displayed in the fifth position 135, the area setting unit 216 sets a corresponding area A5 corresponding to the target image M in the fifth position 135. The area setting unit 216 sequentially switches the setting of the corresponding area A from the corresponding area A1 to the corresponding area A5 in synchronization with the sets of timing at which the position of display of the target image M switches sequentially from the first position 131 to the fifth positions 135.

As described above, in each of the display periods in which the target image M is displayed, the image data acquisition unit 206 acquires the image data on the left and right eyeballs, the position detector 210 detects the positional data of the pupil center and the positional data of the center of corneal reflection, and the point-of-regard detector 214 calculates the positional data of the point of regard. The process is performed according to the period of the frame synchronization signal that is, for example, output from the first camera 102A and the second camera 102B (for example, every 50 [msec]). The first camera 102A and the second camera 102B capture images synchronously.

Figure 9:
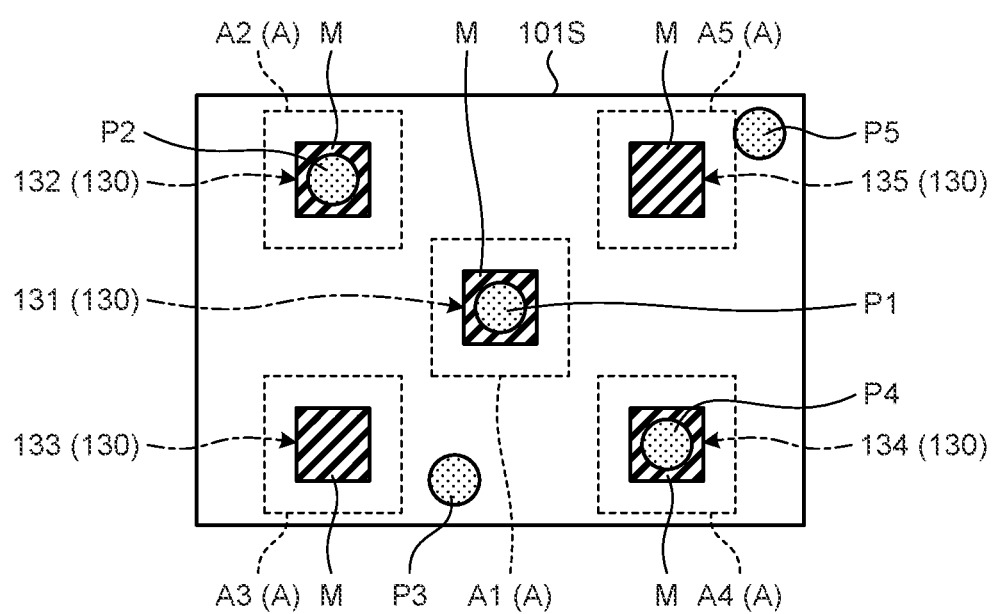
FIG. 9 is a diagram illustrating an example of detection areas where points of regard are detected by a calibration operation.

FIG. 9 is a diagram illustrating an example of detection areas where points of regard are detected by the calibration operation. Detection areas P1 to P5 illustrated in FIG. 9 schematically illustrate areas of detected points of regard in the respective display periods in which the target image M is displayed in the first to fifth positions 131 to 135. The points of regard that are calculated by the calibration operation are not displayed on the display screen 101S practically.

The calibration controller 222 determines, on each of the target images M, whether the positional data of the point of regard that is calculated in the above-described calibration operation is present within the corresponding area A. As illustrated in FIG. 9, in the display period in which the target image M is displayed in the first position 131, the area of the calculated point of regard is present within the corresponding area A1. Thus, the calibration controller 222 determines that the positional data of the point of regard is present within the corresponding area A1. In this case, the target image M that is displayed in the first position 131 serves as a valid target image.

In the display period in which the target image M is displayed in the second position 132, the area of the calculated point of regard is present within the corresponding area A2. Thus, the calibration controller 222 determines that the positional data of the point of regard is present within the corresponding area A2. In this case, the target image M that is displayed in the second position 132 serves as a valid target image.

In the display period in which the target image M is displayed in the third position 133, the area of the calculated point of regard is not present within the corresponding area A3. Thus, the calibration controller 222 determines that the positional data of the point of regard is not present within the corresponding area A3. In this case, the target image M that is displayed in the third position 133 does not serve as a valid target image.

In the display period in which the target image M is displayed in the fourth position 134, the area of the calculated point of regard is present within the corresponding area A4. Thus, the calibration controller 222 determines that the positional data of the point of regard is present within the corresponding area A4. In this case, the target image M that is displayed in the fourth position 134 serves as a valid target image.

In the display period in which the target image M is displayed in the fifth position 135, the area of the calculated point of regard is not present within the corresponding area A5. Thus, the calibration controller 222 determines that the positional data of the point of regard is not present within the corresponding area A5. In this case, the target image M that is displayed in the fifth position 135 does not serve as a valid target image.

As a result, in the above-described calibration operation, three valid target images are detected. The calibration controller 222 determines whether the number of the valid target images that are detected as described above is at or above the threshold. The threshold can be set, for example, by the operator by making an input via the input device 60, or the like.

The number of the valid target images is three here and thus, for example, when the threshold is set at or under "3", the calibration controller 222 determines that the number of the valid target images is at or above the threshold. When the number of the valid target images is at or above the threshold, the calibration controller 222 outputs positional data on the points of regard with respect to the valid images as calibration data. In other words, the calibration controller 222 outputs, as calibration data, positional data of the point of regard in the detection area P1 corresponding to the target image M in the first position 131. The calibration controller 222 outputs, as calibration data, positional data of the point of regard in the detection area P2 corresponding to the target image M in the second position 132. The calibration controller 222 outputs, as calibration data, positional data of the point of regard in the detection area P4 corresponding to the target image M in the fourth position 134.

On the other hand, when the threshold is set at or above "4", the calibration controller 222 determines that the number of the valid target images is under the threshold. When the number of the valid target images is under the threshold, the calibration controller 222 causes the calibration operation to be repeated. In this case, the calibration controller 222 stores the positional data of the points of regard that are detected in the above-described calibration operation in the storage 224.

When the calibration operation is caused to be repeated, the display controller 202 displays the target image M in the same target positions 130 as those in the latest calibration operation. In other words, the display controller 202 displays the target image M in the five target positions 130 from the first position 131 to the fifth position 135. The area setting unit 216 sets a corresponding area A in a period in which the target image M is displayed in each target position 130 by the same process as that of the latest calibration operation. The image data acquisition unit 206 acquires image data on the left and right eyeballs, the position detector 210 detects positional data of the pupil center and positional data of the corneal reflection center, and the point-of-regard detector 214 calculates positional data of the point of regard. In this manner, the computer system 20 automatically repeats the calibration operation and thus it is possible to efficiently acquire more natural and accurate measurement results while maintaining concentration of the subject without hindering the flow of the gaze detection process. When repeating the calibration operation, the computer system 20 shifts to the calibration operation without making a notification of the fact, which thus inhibits the concentration of the subject from lapsing.

Figure 10:
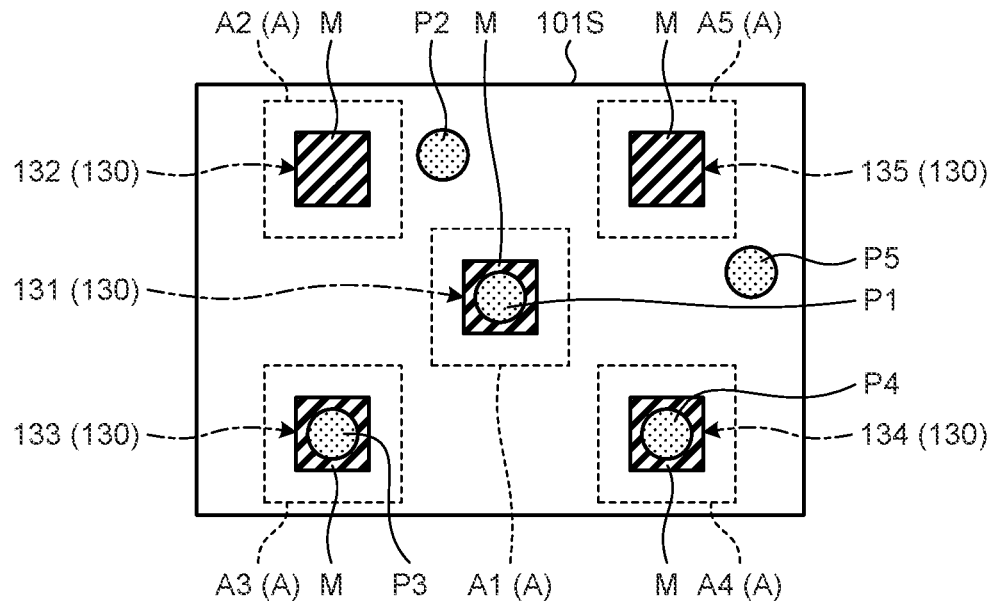
FIG. 10 is a diagram illustrating an example of detection areas where points of regard are detected by the repeated calibration operation.

FIG. 10 is a diagram illustrating an example of detection areas where points of regard are detected by the repeated calibration operation. In the example illustrated in FIG. 10, in the display periods in which the target image M is displayed in the first position 131, the third position 133 and the fourth position 134, the areas of the calculated points of regard are present respectively within the corresponding areas A1, A3 and A4. Thus, in the repeated calibration operation, the three target images that are displayed in the first position 131, the third position 133 and the fourth position 134 are detected as valid target images.

The above-described calibration operation is of a system in which the target image M that is displayed sequentially in the target positions 130 on the display screen 101S is followed and regarded. The inventors found that, in the system, a subject who performs following and regarding correctly is characterized in performing following and regarding in the same way of viewing in each calibration operation. In other words, when distribution of positional data of the points of regard coincides or similar among the multiple numbers of calibration operation, it can be estimated that the subject views in the same manner. For this reason, when the target image M that is displayed in the same position as that of the target image M that is determined as a valid target image in the repeated calibration operation is successively determined as a valid target image in the latest calibration operation or a calibration operation before the latest calibration, it can be considered that the subject views in the same manner.

Thus, when causing the calibration operation to be repeated, the calibration controller 222 stores positional data of a center point that is calculated in the latest calibration operation in the storage 224 with respect to each target position 130. The calibration controller 222 then displays the target image M in the same target positions 130 as those in the latest calibration operation, that is, each of the first to fifth positions 131 to 135. Thereafter, when the target image M that is displayed in the target position 130 that is the same between the repeated calibration operation and the latest calibration operation or a calibration operation before the latest calibration operation is successively determined as a valid target image, the calibration controller 222 determines other all valid target images in the latest calibration operation or a calibration operation before the latest calibration operation among the successive calibration operations as valid target images in the repeated calibration operation.

In the calibration operation illustrated in FIG. 9 and the repeated calibration operation illustrated in FIG. 10, two target images M that are displayed in the first position 131 and the fourth position 134 are detected as valid target images together. Accordingly, the calibration controller 222 determines that other all valid target images in the latest calibration operation are valid target images in the repeated calibration operation. In other words, the target image M that is displayed in the second position 132 and that is determined as a valid target image in the latest calibration operation is also detected as a valid target image in the repeated calibration operation. As a result, in the calibration operation illustrated in FIG. 10, four valid target images are detected.

When the repeated calibration operation illustrated in FIG. 10 is performed and then the further repeated calibration operation is performed (referred to as the further repeated calibration operation below), the calibration controller 222 stores positional data of a center point that is calculated in the latest calibration operation in the storage 224 with respect to each target position 130. The calibration controller 222 then displays the target image M in each of the first to fifth positions 131 to 135. Thereafter, when, at least one of the target images M that are displayed in the first position 131 and the fourth position 134 that are the same target positions 130 as those in the latest two calibration operations is determined as a valid target image, the calibration controller 222 determines other all valid target images in the two calibration operations as valid target images in the further repeated calibration operation.

As described above, the calibration controller 222 stores the positional data of the point of regard that is calculated in each calibration operation and, when a valid target image in the repeated calibration operation is determined, uses the positional data of the point of regard that is stored in the storage as feedback data.

The calibration controller 222 determines whether the number of the valid target images detected as described above is at or above the threshold and, when the number of the valid target images is at or above the threshold, outputs positional data on the points of regard with respect to the valid target images as calibration data. When the number of the valid target images is under the threshold, the calibration controller 222 causes the calibration operation to be repeated.

Figure 11:
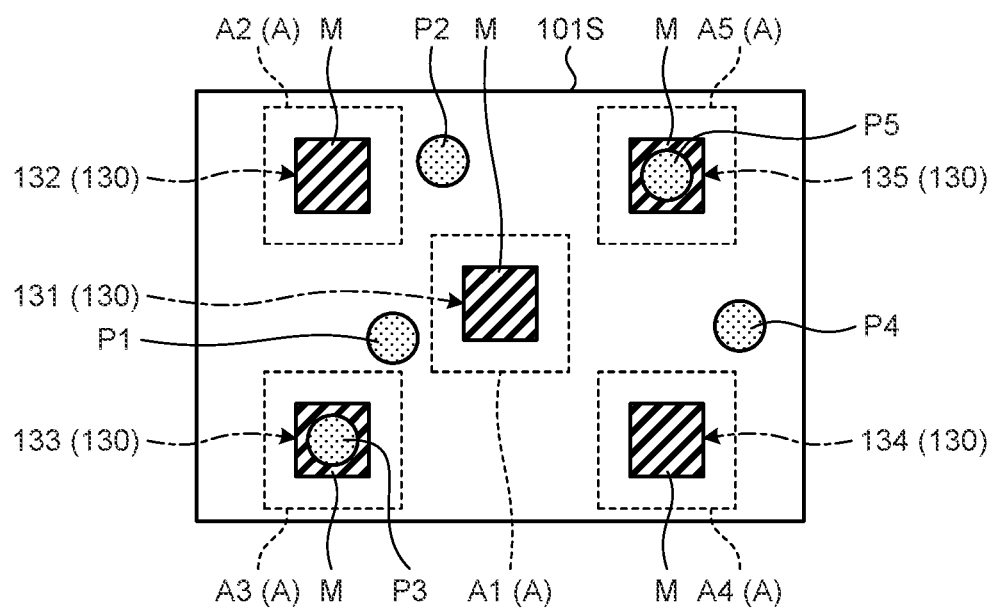
FIG. 11 is a diagram illustrating another example of the detection areas where points of regard are detected by the repeated calibration operation.

FIG. 11 is a diagram illustrating another example of the detection areas where points of regard are detected by the repeated calibration operation. In the example illustrated in FIG. 11, in the display period in which the target image M is displayed in the third position 133 and the fifth position 135, the areas of the calculated points of regard are present within the corresponding areas A3 and A5, respectively. Thus, in the repeated calibration operation, the two target images M that are displayed in the third position 133 and the fifth position 135 are detected as valid target images.

On the other hand, in the repeated calibration operation illustrated in FIG. 11, there is no valid target image that is detected at the same position as that in the calibration operation illustrated in FIG. 9 that is the latest calibration operation. Thus, in this case, the calibration controller 222 does not determine the valid target images in the latest calibration operation as valid target images in the repeated calibration operation. As a result, in the calibration operation illustrated in FIG. 11, two valid target images are detected.

Figure 12:
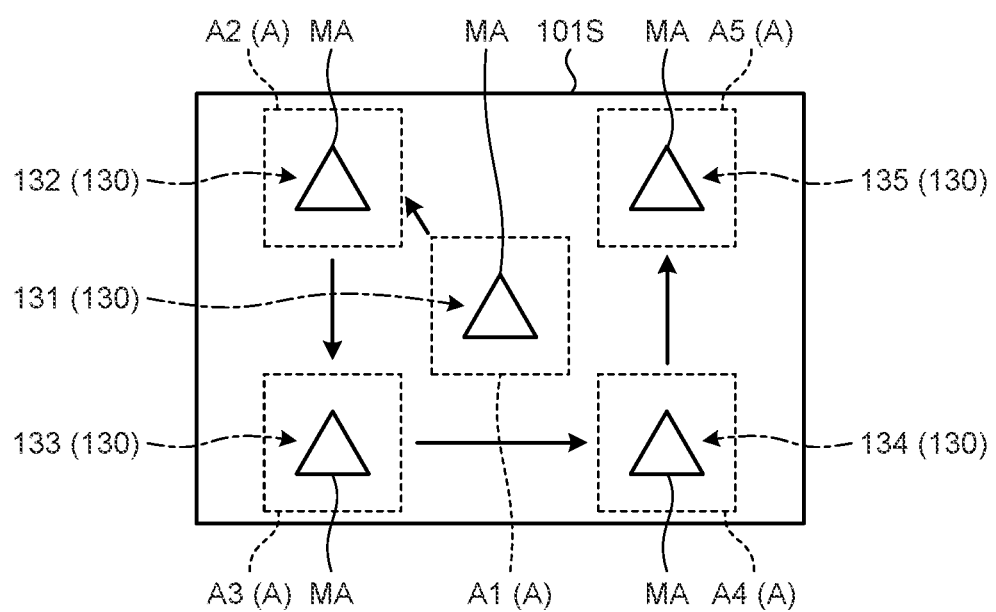
FIG. 12 is a diagram illustrating another display example in which a target image is displayed on the display screen.

In the example illustrated in FIGS. 10 and 11, the mode in which, when performing the repeated calibration operation, the display controller 202 displays the target image whose appearance is the same as the target image M displayed in the latest calibration operation has been described; however, the calibration operation is not limited to this. FIG. 12 is a diagram illustrating another display example in which the target image is displayed on the display screen 101S. As illustrated in FIG. 12, when causing the calibration operation to be repeated, the display controller 202 is able to display a target image MA whose appearance differs from that of the target image M that is displayed in the latest calibration operation. In this case, the display controller 202 displays the target image M in the same target positions 130 as those in the latest calibration operation. In this manner, displaying the target image MA whose appearance differs from that of the target image M in the latest calibration operation makes it possible to inhibit the concentration and regarding rate of the subject from lowering because the subject gets bored.

When the above-described calibration is performed for a given number of times and the number of target images is under the threshold in every calibration operation, the calibration controller 222 makes an output indicating that the calibration operation is erroneous. The given number of times can be set, for example, by the operator by making an input via the input device 60, or the like.

Figure 13:
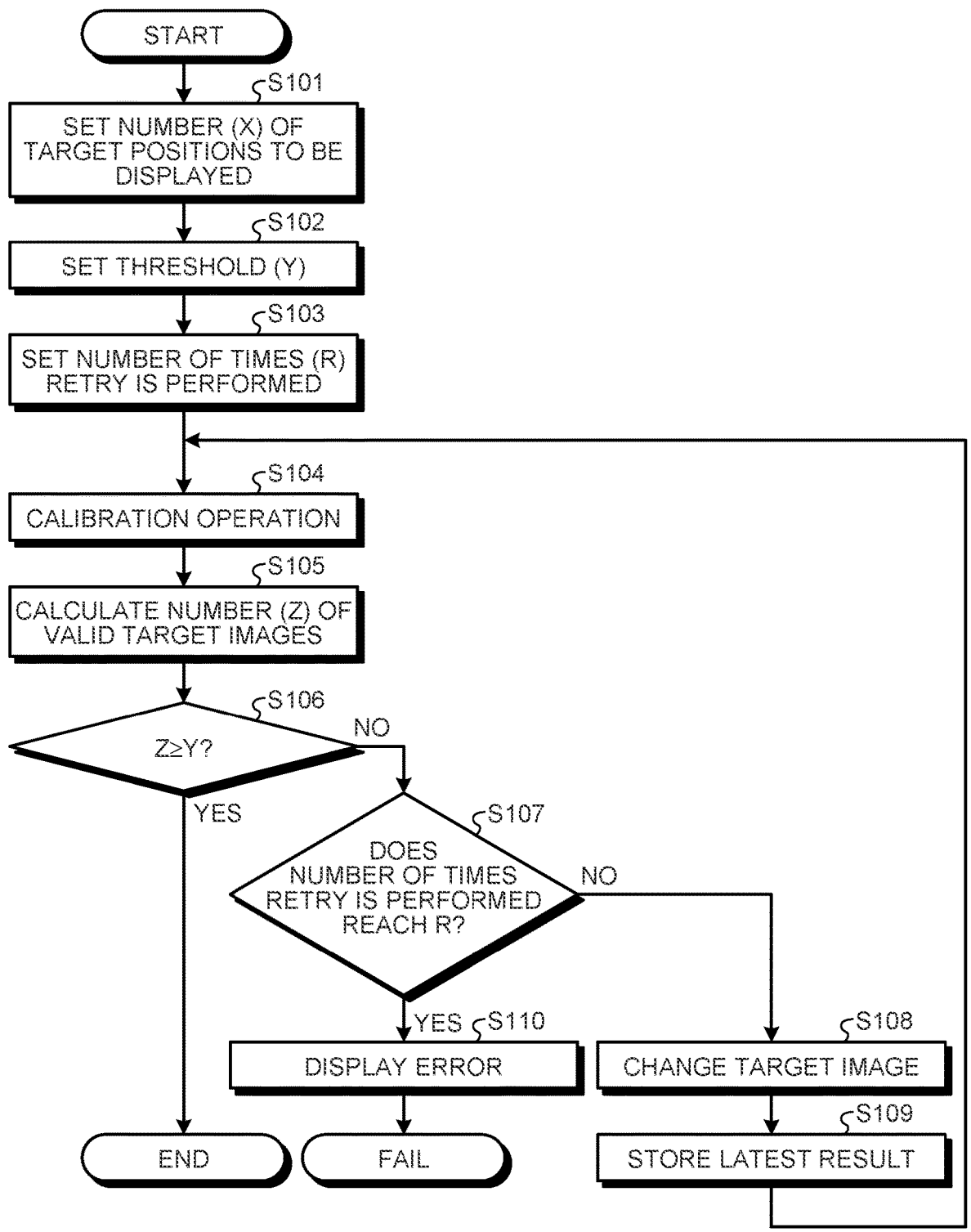
FIG. 13 is a flowchart illustrating the example of the calibration process in a gaze detection method according to the embodiment.

The example of the gaze detection method according to the embodiment will be described with reference to FIG. 13. FIG. 13 is a flowchart illustrating an example of the calibration process in the gaze detection method according to the embodiment. As illustrated in FIG. 13, first of all, the calibration controller 222 sets a number (X) of the target positions 130 that are displayed on the display screen 101S (step S101). The calibration controller 222 sets the number X of the target positions 130 based on a result of an input in the input device 60. Note that X is an integer that is 2 or larger.

The calibration controller 222 sets a threshold (Y) of valid target images (step S102). The calibration controller 222 sets the threshold Y of valid target images based on a result of an input in the input device 60. Note that Y is an integer that is 1 or larger or X or smaller.

The calibration controller 222 sets a number of retries (R) in which the repeated calibration operation is performed (step S103). The calibration controller 222 sets the number of retries R based on, for example, the result of an input in the input device 60. Note that R is an integer that is 1 or larger. Note that R may be 0. In this case, a setting is made such that the repeated calibration is not performed.

After the number X of the target positions 130, the threshold Y of valid target images, and the number of times R the repeated calibration operation is performed are set, the calibration operation is caused to be performed (step S104). In the calibration operation, a target image M is displayed in the multiple target positions 130 based on the set number X of the target positions 130 and corresponding areas A corresponding to the target images M are set in the periods in which the target images M are displayed, respectively. In the display period in which the target image M is displayed, the image data acquisition unit 206 acquires image data on the left and right eyeballs, the position detector 210 detects positional data of the pupil center and positional data on the corneal reflection center, and the point-of-regard detector 214 calculates positional data of the point of regard.

After the calibration operation, the calibration controller 222 calculates a number (Z) of the target images M that are determined as valid target images (step S105). At step S105, when the target image M that is displayed in the same target position 130 between the repeated calibration operation and the latest calibration operation or a calibration operation before the latest calibration operation is successively determined as a valid target image, the calibration controller 222 determines other all valid target images in the latest calibration operation or a calibration operation before the latest calibration operation among the successive calibration operations as valid target images in the repeated calibration operation. After calculating the number Z of the valid target images, the calibration controller 222 determines whether the number Z of the valid target images is at or above the threshold Y (step S106). When it is determined that the number Z of the valid target images is at or above the threshold Y (YES at step S106), the calibration controller 222 outputs the positional data of the points of regard on which valid target images are determined as calibration data and ends the calibration operation.

On the other hand, when it is determined that the number Z of the valid target images is under the threshold Y (NO at step S106), the calibration controller 222 determines whether the number of retries in which the repeated calibration operation is performed until the determination reaches the set number of retries R (step S107). When the number of retries of the calibration operation reaches the set number R as a result of the determination (YES at step S107), the calibration controller 222 makes an output indicating that the calibration operation is erroneous (step S110) and ends the process.

When the number of retries of the calibration operation does not reach the set number R (NO at step S107), the calibration controller 222 causes the repeated calibration operation to be performed. In the repeated calibration operation, when the type of target image M is changed to a target image with different appearance, the calibration controller 222 transmits an instruction to change the type of target image M to the display controller 202 (step S108). In this case, in the repeated calibration operation, a target image whose appearance differs from that in the latest calibration operation is displayed on the display screen 101S. When causing the repeated calibration operation to be performed, the calibration controller 222 stores positional data on points of regard that is a detection result of the latest calibration operation in the storage 224 (step S109). Thereafter, the operation at and after step S104 is caused to be performed repeatedly.

As described above, the gaze detection apparatus according to the embodiment includes the display screen 101S on which an image is displayed; the illumination device 103 that applies detection light to at least one of eyeballs of a subject; the image data acquisition unit 206 that acquires image data on the eyeball to which the detection light is applied; the position detector 210 that detects, from the acquired image data, positional data of a pupil center representing the center of a pupil of the eyeball to which the detection light is applied and positional data of a corneal reflection center representing the center of corneal reflection; the point-of-regard detector 214 that calculates, based on the position of the pupil center and the position of the corneal reflection center, positional data of a point of regard of the subject on a plane containing the display screen 101S; and the computer system 20 that performs a calibration operation including displaying a target image M in multiple target positions 130 on the display screen 101S sequentially, sequentially setting, in the display screen 101S, corresponding areas A corresponding to the target images M displayed on the display screen 101S, and calculating positional data of the points of regard in display periods in which the respective target images M are displayed, determines, with respect to each of the target images M, whether the positional data of the point of regard that is calculated in the calibration operation is present within the corresponding area A, when a number Z of valid target images that are target images M on each of which it is determined that the positional data of the point of regard is present within the corresponding area A is at or above a threshold Y, outputs the positional data of the points of regard with respect to the valid target images as calibration data, and, when the number Z of the valid target images is under the threshold Y, causes the calibration operation to be repeated.

The gaze detection method according to the embodiment includes: applying detection light to at least one of eyeballs of a subject; acquiring image data on the eyeball to which the detection light is applied; detecting, from the acquired image data, positional data of a pupil center representing the center of a pupil of the eyeball to which the detection light is applied and positional data of a corneal reflection center representing the center of corneal reflection; calculating, based on the position of the pupil center and the position of the corneal reflection center, positional data of a point of regard of the subject on a plane containing the display screen 101S; and the computer system 20 that performs a calibration operation including displaying a target image M in multiple target positions 130 on the display screen 101S sequentially, sequentially setting, in the display screen 101S, corresponding areas A corresponding to the target images M displayed on the display screen 101S, and calculating positional data of the points of regard in display periods in which the respective target images M are displayed, determining, with respect to each of the target images M, whether the positional data of the point of regard that is calculated in the calibration operation is present within the corresponding area A, when a number Z of valid target images that are target images M on each of which it is determined that the positional data of the point of regard is present within the corresponding area A is at or above a threshold Y, outputting the positional data of the points of regard with respect to the valid target images as calibration data, and, when the number Z of the valid target images is under the threshold Y, causing the calibration operation to be repeated.

The gaze detection program according to the embodiment causes a computer to perform a process including: applying detection light to at least one of eyeballs of a subject; acquiring image data on the eyeball to which the detection light is applied; detecting, from the acquired image data, positional data of a pupil center representing the center of a pupil of the eyeball to which the detection light is applied and positional data of a corneal reflection center representing the center of corneal reflection; calculating, based on the position of the pupil center and the position of the corneal reflection center, positional data of a point of regard of the subject on a plane containing the display screen 101S; and the computer system 20 that performs a calibration operation including displaying a target image M in multiple target positions 130 on the display screen 101S sequentially, sequentially setting, in the display screen 101S, corresponding areas A corresponding to the target images M displayed on the display screen 101S, and calculating positional data of the points of regard in display periods in which the respective target images M are displayed, determining, with respect to each of the target images M, whether the positional data of the point of regard that is calculated in the calibration operation is present within the corresponding area A, when a number Z of valid target images that are target images M on each of which it is determined that the positional data of the point of regard is present within the corresponding area A is at or above a threshold Y, outputting the positional data of the points of regard with respect to the valid target images as calibration data, and, when the number Z of the valid target images is under the threshold Y, causing the calibration operation to be repeated.

Because of such a configuration, the computer system 20 automatically performs the repeated calibration operation and thus it is possible to efficiently acquire more natural and accurate measurement results while maintaining concentration of the subject without hindering the flow of the gaze detection process. Thus, it is possible to inhibit the detection accuracy from lowering.

When causing the calibration operation to be repeated, the calibration controller 222 displays the target image M in each of the first to fifth positions 131 to 135 that are the same target positions 130 as those of the latest calibration operation and, when the target image M that is displayed in the target position 130 that is the same between the repeated calibration operation and the latest calibration operation or a calibration operation before the latest calibration operation is determined as a valid target image successively, determines other all valid target images in the latest calibration operation or the calibration operation before the latest calibration operation among the successive calibration operations as valid target images in the repeated calibration operation. Accordingly, using the characteristics of the subject makes it possible to perform an efficient calibration operation.

When causing the calibration operation to be repeated, the calibration controller 222 displays the target image MA whose appearance differs from that of the target image M that is displayed in the latest calibration operation. This makes it possible to inhibit the concentration and regarding rate of the subject from lowering because the subject gets bored.

When the calibration operation is performed for a given number of time R and the number Z of valid target images is under the threshold Y in every calibration operation, the calibration controller 222 makes an output indicating that the calibration operation is erroneous. Thus, when the number Z of valid target images is under the threshold Y even when the repeated calibration operation is performed for the given number of times R, it is possible to close the calibration operation.

The embodiments of the disclosure have been described, and the content of the embodiments does not limit embodiments. The components described above contain ones easily assumed by those skilled in the art and ones substantially the same, that is, ones in the range of equivalence. Furthermore, the above-described components can be combined as appropriate. Furthermore, various omissions, replacements and changes can be made on the components within the scope of the embodiments described above.

According to the disclosure, it is possible to provide a gaze detection apparatus, a gaze detection method, and a gaze detection program that make it possible to inhibit accuracy of detection from lowering.

What is claimed is:

1. A gaze detection apparatus comprising:
    a display screen on which an image is displayed;
    a light source configured to apply detection light to at least one of eyeballs of a subject;
    an image data acquisition unit configured to acquire image data on the eyeball to which the detection light is applied;
    a position detector configured to detect, from the acquired image data, positional data of a pupil center representing a center of a pupil of the eyeball to which the detection light is applied and positional data of a corneal reflection center representing a center of corneal reflection;
    a point-of-regard detector configured to calculate, based on a position of the pupil center and a position of the corneal reflection center, positional data of a point of regard of the subject on a plane containing the display screen; and
    a controller configured to perform a calibration operation including displaying a target image in multiple positions on the display screen sequentially, setting, in the display screen, corresponding areas corresponding to the target images displayed on the display screen sequentially, and calculating positional data of the points of regard in display periods in which the respective target images are displayed; determine, with respect to each of the target images, whether the positional data of the point of regard that is calculated in the calibration operation is present within the corresponding area; when the number of valid target images that are the target images on each of which it is determined that the positional data of the point of regard is present within the corresponding area is at or above a threshold, output the positional data of the points of regard of the valid target images as calibration data; and, when the number of the valid target images is under the threshold, cause the calibration operation to be repeated.

2. The gaze detection apparatus according to claim 1, wherein the controller is configured to, when causing the calibration operation to be repeated, display the target image in each of the same multiple positions as those in the latest calibration operation and, when the target image that is displayed in the position that is the same between the repeated operation and the latest calibration operation or a calibration operation before the latest calibration operation is determined as the valid target image successively, determine other all valid target images in the latest calibration operation or the calibration operation before the latest calibration operation among the successive calibration operations as the valid target images in the repeated calibration operation.

3. The gaze detection apparatus according to claim 1, wherein the controller is configured to, when causing the calibration operation to be repeated, display a target image whose appearance differs from that of the target image that is displayed in the latest calibration operation.

4. The gaze detection apparatus according to claim 1, wherein the controller is configured to, when the calibration operation is performed for a given number of times and the number of the valid target images is under the threshold in every calibration operation, makes an output indicating that the calibration operation is erroneous.

5. A gaze detection method comprising:
    applying detection light to at least one of eyeballs of a subject;
    acquiring image data on the eyeball to which the detection light is applied;
    detecting, from the acquired image data, positional data of a pupil center representing a center of a pupil of the eyeball to which the detection light is applied and positional data of a corneal reflection center representing a center of corneal reflection;

calculating, based on a position of the pupil center and a position of the corneal reflection center, positional data of a point of regard of the subject on a plane containing a display screen; and performing a calibration operation including displaying a target image in multiple positions on the display screen sequentially, setting, in the display screen, corresponding areas corresponding to the target images displayed on the display screen sequentially, and calculating positional data of the points of regard in display periods in which the respective target images are displayed; determining, with respect to each of the target images, whether the positional data of the point of regard that is calculated in the calibration operation is present within the corresponding area; when the number of valid target images that are the target images on each of which it is determined that the positional data of the point of regard is present within the corresponding area is at or above a threshold, outputting the positional data of the points of regard of the valid target images as calibration data; and, when the number of the valid target images is under the threshold, causing the calibration operation to be repeated.

6. A non-transitory computer readable recording medium storing therein a gaze detection program that causes a computer to execute a process including:

applying detection light to at least one of eyeballs of a subject;

acquiring image data on the eyeball to which the detection light is applied;

detecting, from the acquired image data, positional data of a pupil center representing a center of a pupil of the eyeball to which the detection light is applied and positional data of a corneal reflection center representing a center of corneal reflection;

calculating, based on a position of the pupil center and a position of the corneal reflection center, positional data of a point of regard of the subject on a plane containing a display screen; and performing a calibration operation including displaying a target image in multiple positions on the display screen sequentially, setting, in the display screen, corresponding areas corresponding to the target images displayed on the display screen sequentially, and calculating positional data of the points of regard in display periods in which the respective target images are displayed; determining, with respect to each of the target images, whether the positional data of the point of regard that is calculated in the calibration operation is present within the corresponding area; when the number of valid target images that are the target images on each of which it is determined that the positional data of the point of regard is present within the corresponding area is at or above a threshold, outputting the positional data of the points of regard of the valid target images as calibration data; and, when the number of the valid target images is under the threshold, causing the calibration operation to be repeated.

* * * * *